US006376663B1

(12) United States Patent
Williams et al.

(10) Patent No.: US 6,376,663 B1
(45) Date of Patent: *Apr. 23, 2002

(54) DESALTING AND PURIFICATION OF OLIGOSACCHARIDES AND THEIR DERIVATIVES

(75) Inventors: Keith Leslie Williams, Frenchs Forest; Nicolle Hannah Packer, Gordon; John William Redmond, Dickson; Andrew Arthur Gooley, Eastwood, all of (AU)

(73) Assignee: MacQuarie Research Ltd., New South Wales (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,539
(22) PCT Filed: Nov. 29, 1996
(86) PCT No.: PCT/AU96/00769
§ 371 Date: Feb. 17, 1999
§ 102(e) Date: Feb. 17, 1999
(87) PCT Pub. No.: WO97/20853
PCT Pub. Date: Jun. 12, 1997

(30) Foreign Application Priority Data

Dec. 1, 1995 (AU) ............................................ PN 6948

(51) Int. Cl.⁷ ............................ C07H 1/06; C07H 1/00; C07H 3/00; B01D 15/08
(52) U.S. Cl. ........................ 536/127; 536/124; 210/656; 210/660; 423/448
(58) Field of Search ................................. 536/124, 127; 423/448; 210/656, 660

(56) References Cited

U.S. PATENT DOCUMENTS 2,549,840 A    4/1951   Montgomery et al. ......... 127/55
5,431,821 A  * 7/1995   Olesik et al. ................ 210/365

OTHER PUBLICATIONS

Davies et al., High Performance liquid . . . , J. of Chromatography, v. 609, pp. 125–131, 1992.*
Fan et al., High Performance liquid . . . , Analytical Biochem., v. 219, pp. 224–229, 1994.*

Journal of Chromatography; v.646 (1993) pp. 317–326; M. J. Davies et al., "Use of a porous graphitized carbon column for the high performance liquid chromatography of oligosaccharides, alditols and glycopeptides with subsequent mass spectrometry analysis".

The Carbohydrates—Chemistry and Biochemistry; Pigman, W. and Horton, D. W/Editors Vol. 11A, second Edition, 1970 academic Press; p. 85.

Analytical Biochemistry vol. 219 (1994) pp. 224–229; Jian Qiang Fan, et al., "High–performance Liquid Chromatography of glycopeptides and oligosaccharides on Graphitized Carbon Columns".

Analytical Sciences Vol. 8 (Dec. 1992) pp. 793–797; Mada, Akira et al. "Utility of a Carbon Column for High–Performance Liquid Chromatographic Separation of Unsaturated Disaccharides Produced from Glycosaminoglycans".

Carbohydrate Research Vol. 215 (1991) pp. 67–80; Kyoko Koizumi et al. "High–performance liquid chromatography of mono–and oligo–saccharides on a graphitized carbon column".

Chemical Abstracts Vol. 118, No. 9 issued Mar. 15 1993. Columbus Ohio USA, p. 390 column 1 abstract No. 76596. Koizumi, Kyoko et al. JPN Kokai Tokyo Koho JP 04297868 [92297868] (C1 G01N 30/88) Oct. 21 1992, Appln. No. 91/874227 Mar. 1991.

Whistler, R.L. et al., "Methods of Carbohydrates Chemistry", Vol. 1, 1962, pp. 42–44.

* cited by examiner

Primary Examiner—Gary Geist
Assistant Examiner—Howard Owens
(74) Attorney, Agent, or Firm—Morgan, Lewis & Bockius LLP

(57) ABSTRACT

A preparative method of separating oligosaccharides from contaminants such as peptides and salts, comprising the steps of reacting a solution containing oligosaccharides and contaminants with a solid support comprising graphitized carbon such that the oligosaccharides substantially bind to the solid support; washing the support to remove any contaminants not bound to the solid support; and eluting the bound oligosaccharide from the support without eluting bound contaminants to obtain a solution of oligosaccharides substantially free of contaminants.

18 Claims, 16 Drawing Sheets

DESALTING AND PURIFICATION OF OLIGOSACCHARIDES AND THEIR DERIVATIVES

TECHNICAL FIELD

The present invention relates to methods for purifying sugars in particular methods for desalting oligosaccharides and their derivatives.

BACKGROUND ART

In contrast to proteins which, because of their high molecular weight, are readily desalted by dialysis or gel chromatography, small oligosaccharides are extremely difficult to desalt. Methods which are used include the removal of ions using mixed-bed ion-exchange columns, precipitation of the salt by a non-aqueous solvent or chemical reaction (such as adding barium carbonate to remove sulfuric acid as the insoluble barium sulfate) and by gel chromatography using highly-cross-linked packings (with which separation of small oligosaccharides is difficult to achieve).

Solid-phase extraction cartridges are now commercially available for the extraction of hydrophobic substances from aqueous solution, such as pesticide and hydrocarbon residues in ground water. Most commonly, these contain silica which has been modified by the covalent incorporation of allyl groups (most commonly octadecyl or ODS chains) to confer reversed-phase separation characteristics. Such reversed-phase adsorbents show excellent retention of hydrophobic substances, but have very little affinity for hydrophilic solutes, such as sugars. These cartridges are therefore useful for the removal of salts from hydrophobic substances, but not from sugars.

Activated carbon is a long-established adsorbent for the purification of both gases and liquids. It has also been applied to the preparative chromatographic fractionation of mixtures of oligosaccharides which are obtained by partial hydrolysis of polysaccharides, such as starch (1). In that application, an inert diluent, typically diatomaceous earth, is mixed with the carbon to enable increased flow of the solvent through the column. A solution of the crude hydrolysate is applied to such a 'charcoal-Celite' column and the different oligosaccharides are obtained, in order of increasing size. by elution with water containing increasing proportions of ethanol as an organic modifier. The composition is typically changed on a batch basis, rather than by elution with a gradient of organic modifier.

Activated carbon chromatographic adsorbents have not been used in high-performance liquid chromatography (HPLC) but, with the recent availability of graphitised carbon packings (2) an analogous separation mode has become available. Like the older 'activated carbon' and 'activated charcoal', graphitised carbon has extremely high chemical stability, as well as good mechanical properties.

Porous graphitised carbon is presently manufactured by Shandon HPLC (Cheshire, England) who also markets Hypercarb HPLC columns. Carbograph solid-phase extraction cartridges containing the same packing are available from Alltech Associates Inc (Deerfield, Ill. USA). HPLC separations of oligosaccharides have been reported using the Hypercarb column (3, 4, 5,6).

A hitherto unrecognised aspect is the value of carbon columns for the desalting of oligosaccharide solutions. This fact is surprising, in view of the lack of effective methods for the desalting of oligosaccharides. The present inventors have developed a useful method to remove salts or polypeptides from solutions of oligosaccharides.

DISCLOSURE OF INVENTION

In a first aspect, the present invention consists in a method to separate oligosaccharides from salts comprising the steps of:

(a) reacting an oligosaccharide solution including salts with a solid support comprising carbon such that the oligosaccharides substantially bind to the solid support;

(b) washing the support to remove salts; and (c) eluting the bound oligosaccharides from the support.

In a second aspect, the present invention consists in a method to separate oligosaccharides from polypeptides comprising the steps of:

(a) reacting an oligosaccharide solution including polypeptides with a solid support comprising carbon such that the oligosaccharides substantially bind to the solid support;

(b) washing the support to remove polypeptides; and (c) eluting the bound oligosaccharides from the support.

Preferably, the solid support comprises porous graphitised carbon and the support is packed in a chromatography column or cartridge. In these forms the support can be used in either continuous or batch mode, for clean-up of samples before chromatography, for chromatographic separation or for clean-up after chromatography, especially when samples are to be submitted to spectroscopic analysis. The washing step is preferably with water and the elution step preferably includes an organic modifier. In one preferred form, the organic modifier is acetonitrile. The concentration of organic modifier is preferably from about 1 to 90% v/v. It will be appreciated by one skilled in the art, however, that other organic modifiers are suitable, especially the lower alcohols methanol, ethanol, propanol and butanol.

The bound oligosaccharides can be removed by varying the concentration of the organic modifier during the elution step. Furthermore, in order to separate different oligosaccharides bound to the support, different concentrations of organic modifier can be used in combination with acidic or basic modifiers. A suitable acidic modifier is a dilute acid, for example, trifluoroacetic acid (TFA), preferably at a concentration of about 0.01 to 1% v/v. A suitable basic modifier is ammonia. It will be appreciated, however, that other basic and acidic modifiers would be suitable for the methods of the present invention. The concentration of acidic or basic modifiers is preferably from about 0.01 to 5% v/v. Elution may include increasing the concentration of organic modifier in steps or by gradient. Such elution techniques are well known to one skilled in the art.

The methods of the present invention are particularly useful in removing salts used in biological buffers and reagents, as well as removing polypeptides from sugar solutions. Examples include the salts sodium chloride and potassium chloride, caustic alkali like sodium hydroxide, cationic buffers like Tris, anionic buffers like phosphate and acetate, zwitterionic buffers like HEPES and MOPS, and surfactants like SDS. It will be appreciated by one skilled in the art that the salts listed above are only provided as examples and many other salts can be removed from oligosaccharides using the method of the present invention. Furthermore, other compounds used in the separation and analysis of biological materials that do not fall within the strict chemical definition of "salts" may also be removed from sugars using the methods of the present invention. Examples of such compounds are non-ionic detergents.

Removal of these compounds from sugars is included within the scope of the present invention.

In order that the present invention may be more clearly understood, preferred forms thereof will be described with reference to the following drawings:

BRIEF DESCRIPTION OF DRAWINGS

FIG. 6: HPAEC chromatogram of the re-chromatography of a glucose oligomer (DP6) obtained by preparative HPAEC and desalted using a graphitised carbon cartridge by elution of the salt with water and the oligosaccharide with 25% acetonitrile.

DETAILED DESCRIPTION OF THE INVENTION

Figure 1:
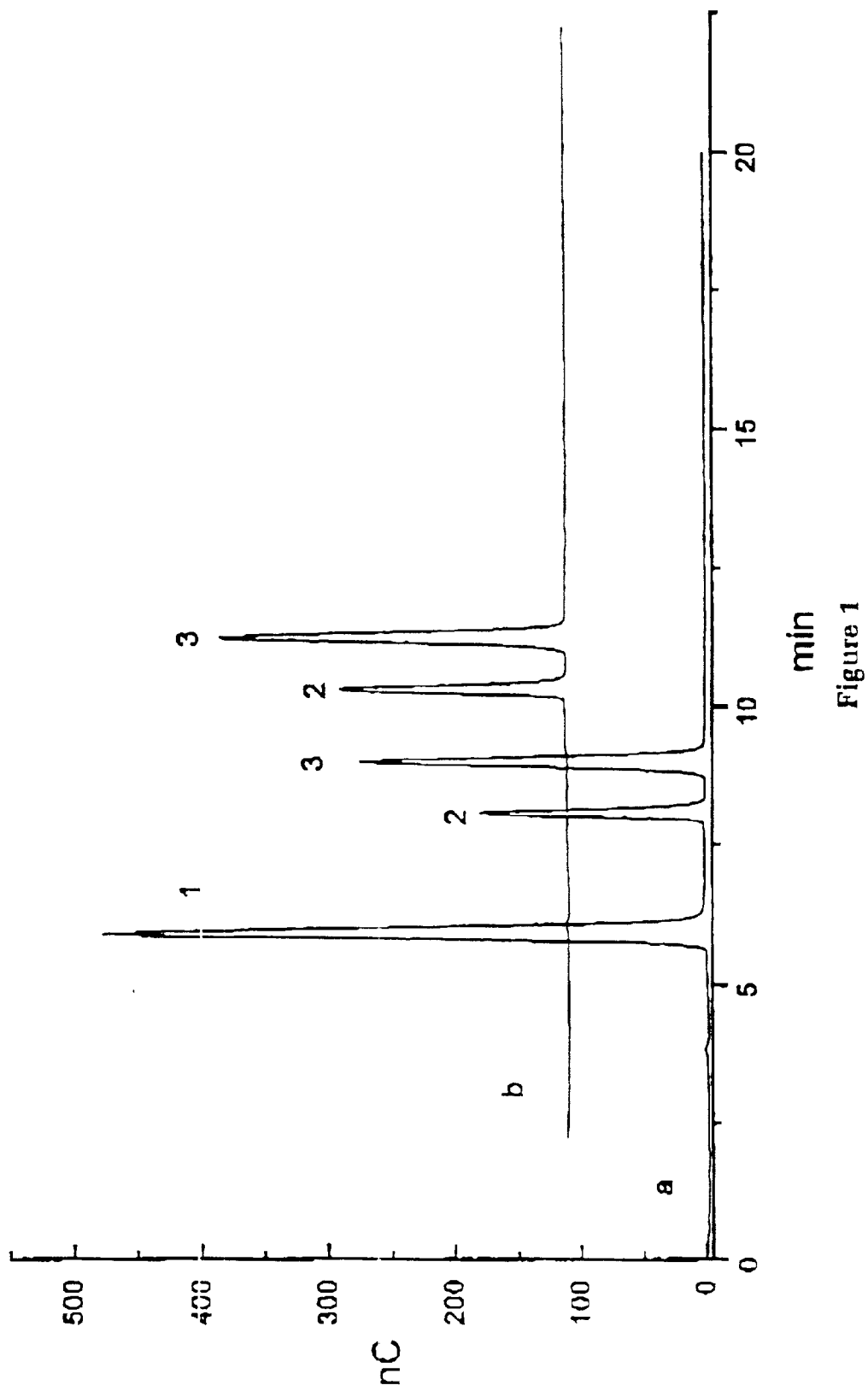
FIG. 1: High performance anion exchange chromatography (HPAEC) chromatogram of the separation of glucose (DP1), maltose (DP2) and raffinose (DP3) in 0.1M sodium chloride.: a) original solution; b) sugars recovered from the graphitised carbon column in 10% acetonitrile in water after an initial elution of the salt with water.

Desalting of the sugar samples is crucial in many techniques of carbohydrate analysis such as mass spectroscopy, capillary electrophoresis, anion exchange chromatography, enzyme degradation and chemical derivatisation.

The present inventors have evaluated graphitised carbon for the isolation of mixtures of oligosaccharides (or their derivatives) from solutions containing one or more of the following contaminants: salt (including caustic alkali), protein (including enzymes), reagents for the release of oligosaccharides from glycoconjugates (such as hydrazine and sodium borohydride) and reagents used for formation of oligosaccharide derivatives (including aromatic amines). Moreover, with the inclusion of either acidic or basic modifiers in the eluents. it is possible to fractionate acidic, phosphorylated, sulphated and neutral oligosaccharides. The adsorbent can be used repeatedly and reproducibly except in the presence of detergents or lipids.

The particular value of this combination of adsorbent properties is in the integration of different chemical, separation and spectroscopic techniques for the preparation, isolation and analysis of the oligosaccharide components of glycoconjugates and complex polysaccharides.

As an illustration, N-linked glycans are released from a glycoprotein by treatment with hydrazine. For the analysis to proceed, it is necessary to separate the glycans from the excess of hydrazine and from the protein and derived peptide hydrazides. This separation is typically achieved by a combination of evaporation (to remove the majority of the hydrazine) and size-exclusion, cellulose or reversed phase chromatography to separate the glycans from the proteinaceous materials. Neither of these procedures is particularly effective. On the other hand, after evaporation of the bulk of the hydrazine, an aqueous solution of the crude product can be applied to a graphitised carbon solid-phase extraction cartridge, then washed with water to remove the remaining hydrazine and then with water (containing up to 25% acetonitrile as an organic modifier) to elute the mixture of neutral glycans, followed with the same eluent containing dilute acid (such as 0.05% trifluoroacetic acid) to elute the acidic glycans. Under these elution conditions, only small peptide hydrazides (formed by the action of the hydrazine on the polypeptide) are coeluted with the glycans. Most of the proteinaceous material is retained by the cartridge.

Alternatively, the glycans may be removed from the glycoprotein by the use of enzymes, such as endoglycanases or glycopeptidases. In this event, it is usually necessary to remove the buffer salts and the enzyme prior to further analysis. The salts are removed by elution of the carbon solid-phase extraction cartridge with water. As before, the glycans remain on the column and are isolated by elution with water-acetonitrile mixtures (with and without the addition of an acid), and the protein is retained by the adsorbent.

The next step in the analysis of the released glycoforms from glycoconjugates is commonly a separation of the glycans using high-performance anion-exchange chromatography at high pH, which involves using an eluent which contains sodium hydroxide and (usually) a gradient of sodium acetate. When the glycan fractions are isolated, they are therefore very alkaline and contain high levels of salt which greatly complicate the analysis of the glycans. The eluent can be desalted using a carbon adsorbent. It is sufficient to neutralise the eluent with acid (either mineral acid or, preferable, an organic acid such as acetic acid), apply the neutralised glycan solution to a column or extraction cartridge containing a carbon adsorbent, elute the salts with water, then elute the glycans with water containing an organic modifier. In an alternative approach, it is not necessary to add acid to neutralise the alkali in the chromatographic eluent. The eluent is simply added to the extraction cartridge, which is then washed well with water to remove inorganic materials and the sugars eluted with water-acetonitrile mixtures as before.

In the publications cited, and in the separation examples outlined below, the organic modifier used with water in the elutions is usually acetonitrile. It should be understood, however, that other modifiers (especially the lower alcohols methanol, ethanol, propanol and butanol) can be used to advantage to obtain improved selectivity and exploit the greater chemical inertness of these solvents.

Oligosaccharide Analysis
Separation of Salt and/or Monosaccharides from Oligosaccharides of DP≧2

Desalting of a mixture of glucose, maltose and raffinose (each 100 μg) in 0.1M sodium chloride (5 mL). The solution was applied to a conditioned graphitised carbon cartridge (washed with several column volumes of 80% acetonitrile:0.1% TFA, followed by re-equilibration with water), which was then rinsed with water (5 mL) and the retained sugars recovered by elution with acetonitrile-water (1:1, 3 mL) (FIG. 1). The recoveries of glucose, maltose and raffinose were 0, 97±2 and 99±2%, respectively as determined by HPAEC-PAD.

Fractionation of Neutral and Acidic Glycans

Figure 2:
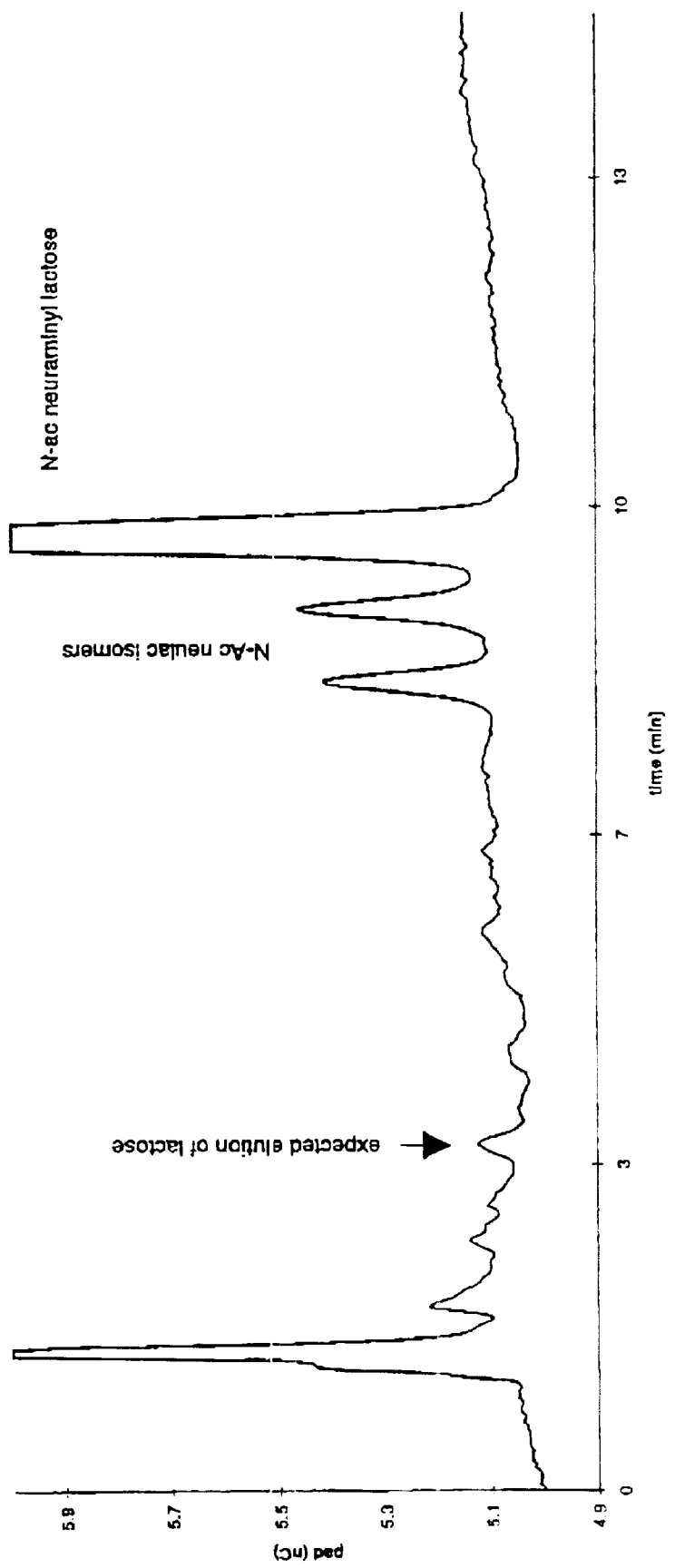
FIG. 2: HPAEC chromatogram of the separation of commercial N-acetylneuraminyllactose eluted from a graphitised carbon cartridge using a 25% acetonitrile eluent containing 0.05% trifluoroacetic acid after preliminary elution of lactose with a 25% acetonitrile eluent without the addition of acid.

To demonstrate the applicability of the graphitised carbon cartridge (PGC) as a one-step process for the separation of neutral and acidic oligosaccharides, a mixture of 1 mg lactose (neutral) and N-acetylneuraminyllactose (acidic) was applied as a water solution to a PGC cartridge. The lactose was eluted with three bed volumes of water containing 10% acetonitrile and the N-acetylneuraminyllactose was then eluted with 0.05% trifluoroacetic acid containing 25% acetonitrile. Eluants were monitored by HPAEC-PAD (FIG. 2) and the neutral lactose was shown to be cleanly separated from the acidic N-acetylneuraminyllactose in one step.

Concentration of Oligosaccharides from a Dilute Solution

A dilute solution of raffinose (DP 3, 1 μg/mL, 100 mL) was allowed to percolate through a conditioned graphitised carbon cartridge at approx. 30 mL/h, and the cartridge then rinsed with water (5×1 mL). The retained raffinose was eluted in acetonitrile/water (1:1, 3 mL). An aliquot (100 μL) of the eluate evaporated in a nitrogen stream, reconstituted in water (100 μL) and the recovery was analysed by HPAEC-PAD and was found to be 98±3%.

To determine the capacity of the column, a solution of raffinose (200 mg) in water (5 mL) was applied to a conditioned graphitised carbon cartridge, the cartridge rinsed with water (5×1 mL) and the retained raffinose eluted with acetonitrile:water (1:1, 5 mL). An aliquot (10 μL) of the eluate was evaporated in a nitrogen stream, reconstituted in water (1 mL) and analysed by HPAEC. The total raffinose recovered in the acetonitrile:water eluate from a column containing 150 mg graphitised carbon was 41±2 mg.

Purification of Oligosaccharides from Acid Reversion of Glucose

Oligosaccharides can be synthesised by heating a concentrated solution of the monomer in acid. Glucose (1 g) was heated at 100° C. for 4 h in 1 ml of 2M TFA and applied to the carbon column. The acid and glucose monosaccharide were washed from the column in 5 mL water and oligomers DP 2 or greater were eluted in 3 mL 25% acetonitrile in water.

Isolation of Oligosaccharides from Corn Syrup

Figure 3A:
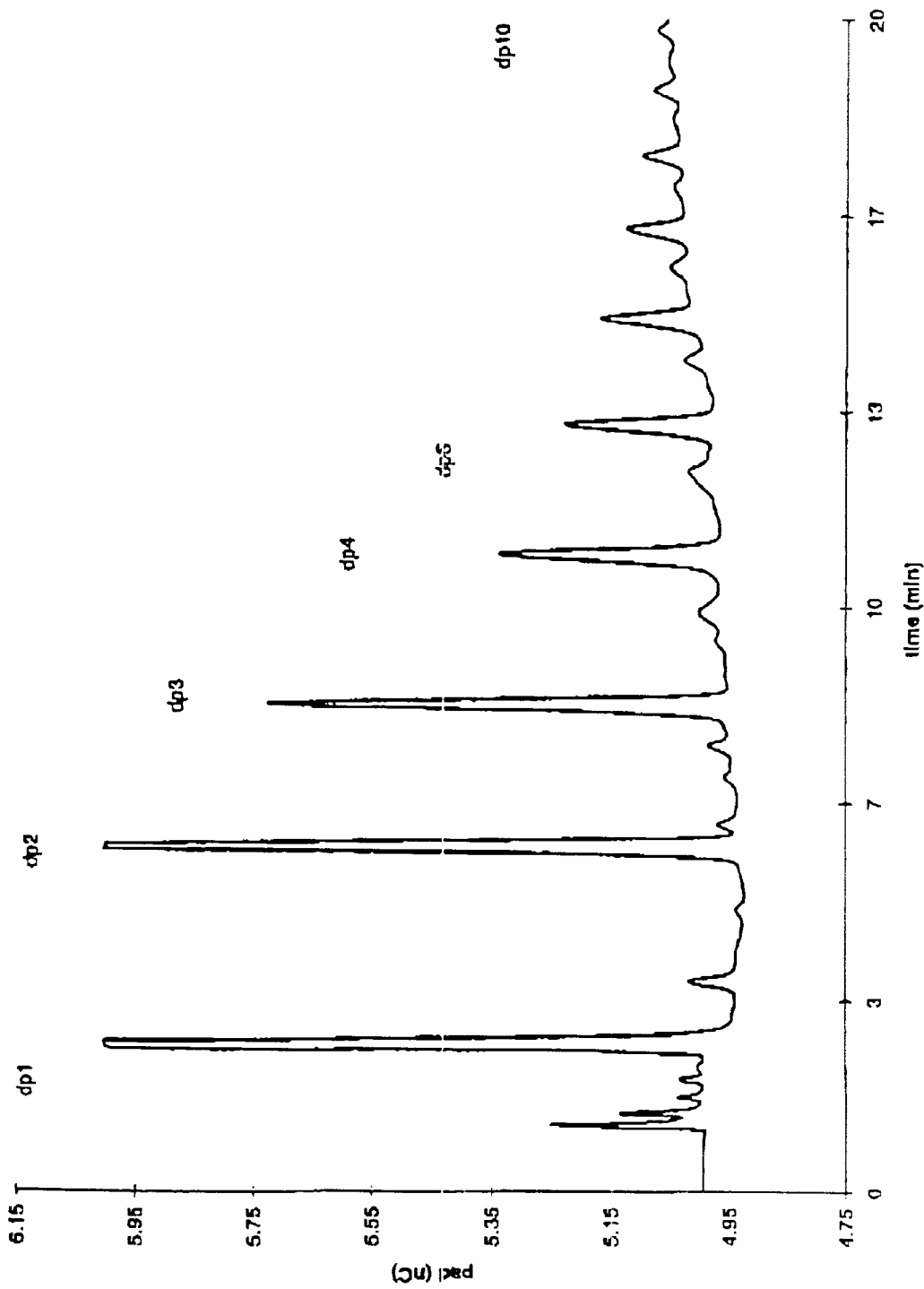
FIG. 3: HPAEC chromatogram of the separation of the oligosaccharides present in a) commercial glucose (corn) syrup; b) the oligosaccharides present in commercial glucose (corn) syrup which are eluted from a graphitised carbon cartridge by a 10% acetonitrile eluent; c) the oligosaccharides present in commercial glucose (corn) syrup which are eluted from a graphitised carbon cartridge by a 25% acetonitrile eluent, after stepwise elution with water and 10% acetonitrile.
Figure 3B:
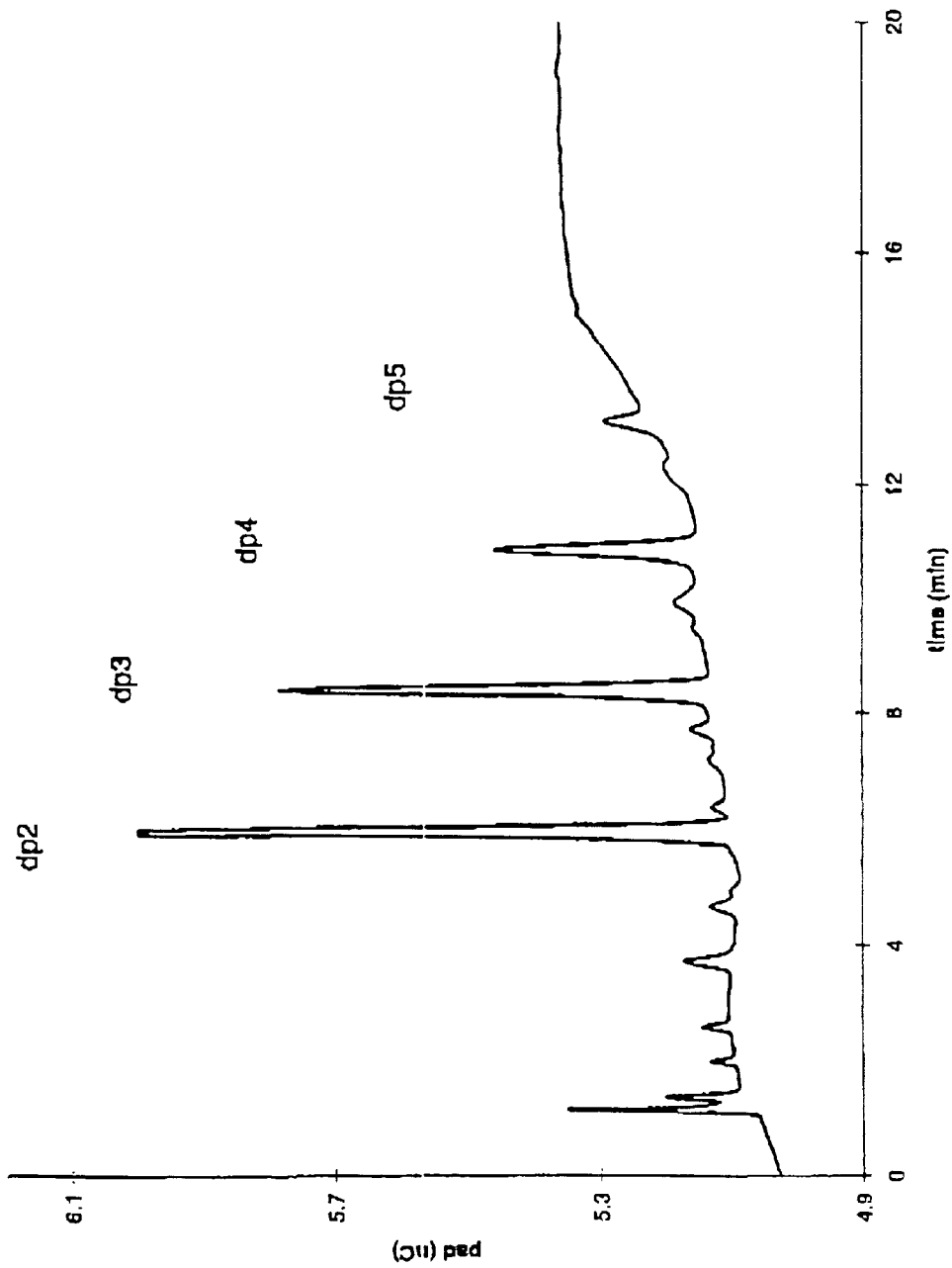
Figure 3C:
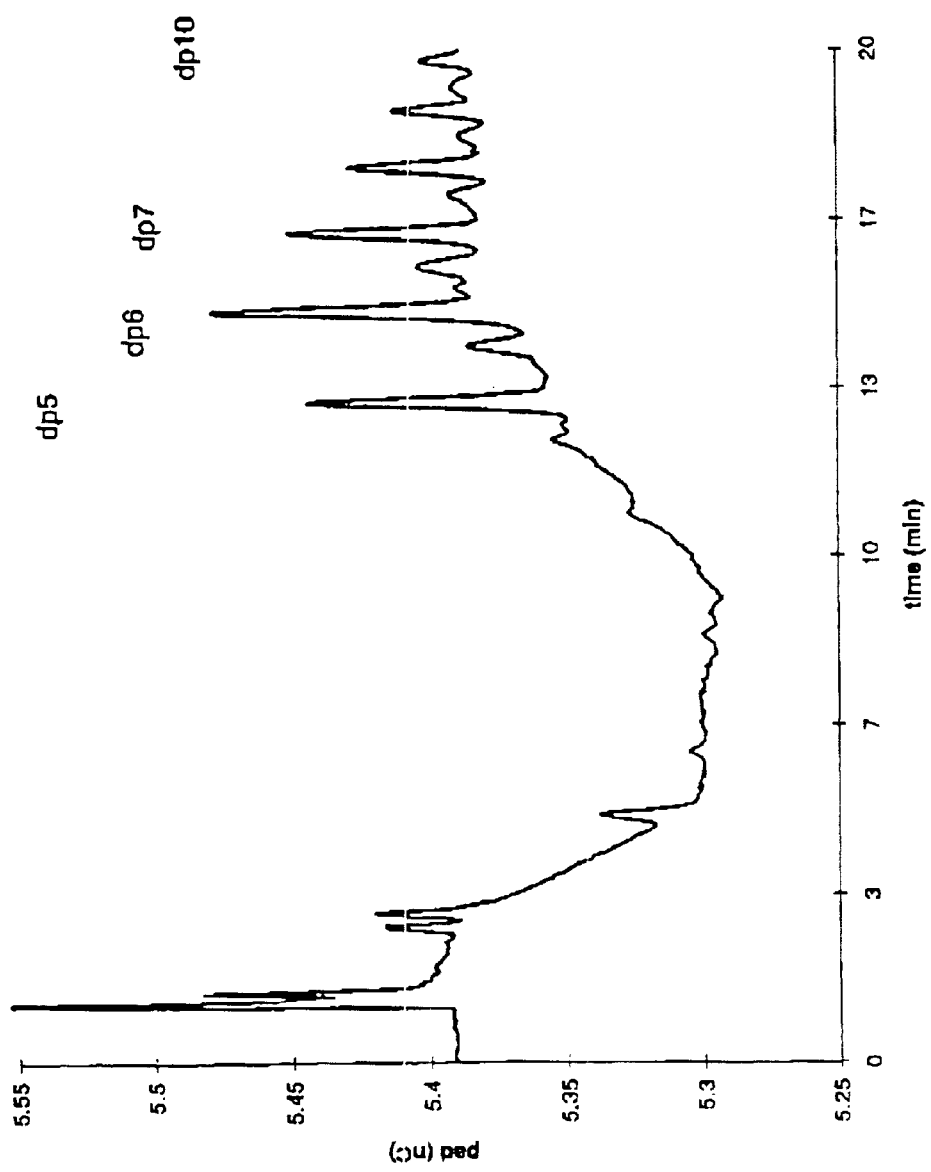

A solution of commercial glucose syrup in water (10 mg in 5 mL) (FIG. 3a) was applied to an extraction cartridge (1 mL) containing graphitised carbon. Washing with five bed volumes (5 mL) of water effected the elution of only glucose and salt. Subsequent batch elution with three bed volumes (3 mL) of water containing 10% and 25% acetonitrile resulted in the elution of oligosaccharides of DP from 2 to 4 (FIG. 3b) and DP from 5 to 10 respectively (FIG. 3c) as monitored by HPAEC.

Removal of Acid After Partial Hydrolysis of Oligosaccharides

Figure 4:
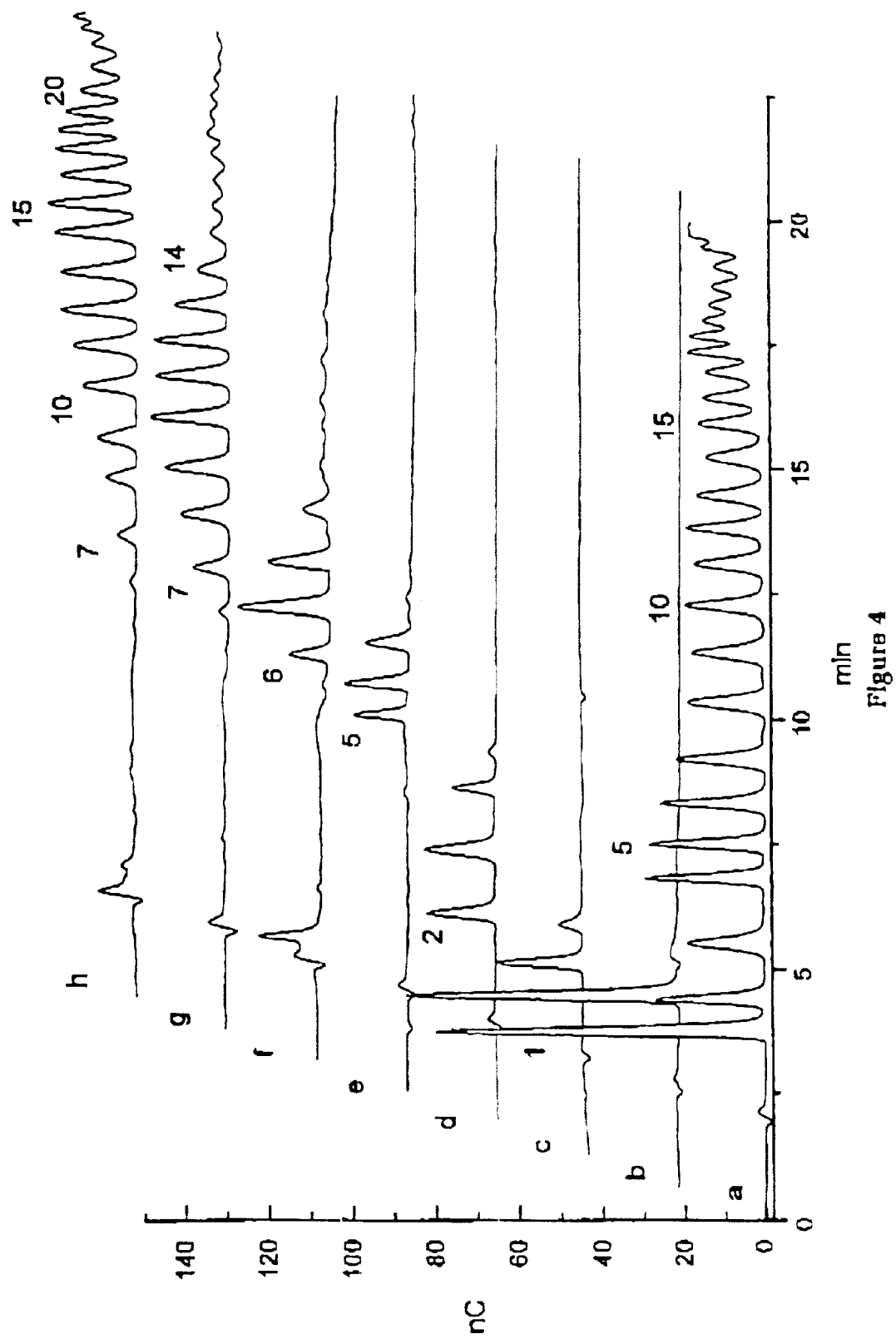
FIG. 4: HPAEC chromatogram of the separation of the oligosaccharides present in a) initial dextran HCl hydrolysate; b) eluate from application to graphitised carbon cartridge; c) water wash of cartridge; d) BSW/16 eluate; e) BSW/8 eluate; f) BSW/4 eluate; g) BSW/2 eluate; and h) BSW eluate. The numeric labels on selected peaks refer to the degree of polymerisation (DP).

Acidic solutions of glycans can be applied to graphitised carbon, such as a hydrolysate of a polysaccharide which still contains the non-volatile acid. The acid and monosaccharides can then be removed by elution with water and the sugar fragments eluted as before with acetonitrile/water with or without added trifluoroacetic acid. Dextran 500 (10 mg) was dissolved in 0.1M hydrochloric acid (100 μL) and heated at 100° C. for 2 hours. The hydrolysate was diluted in water (5 mL) and applied to a conditioned graphitised carbon cartridge. The cartridge was then washed with water (5 mL), and then eluted with a sequence of eluents (each 5 mL) prepared by dilution of BSW (water saturated with 1-butanol) with water. (These eluents are designated BSW/2, BSW/4, BSW/8 and BSW/16 to correspond to two-fold up to 16-fold dilutions of BSW in water) (FIG. 4). It can be seen, for instance, that elution with BSW/8 affords a fraction consisting only of oligosaccharides of DP 5, 6 and 7, while the BSW eluate consists primarily of oligosaccharides of DP 7 to >20.

Purification of Glycan Derivatives (Glycosylpyrazoles)

Figure 5:
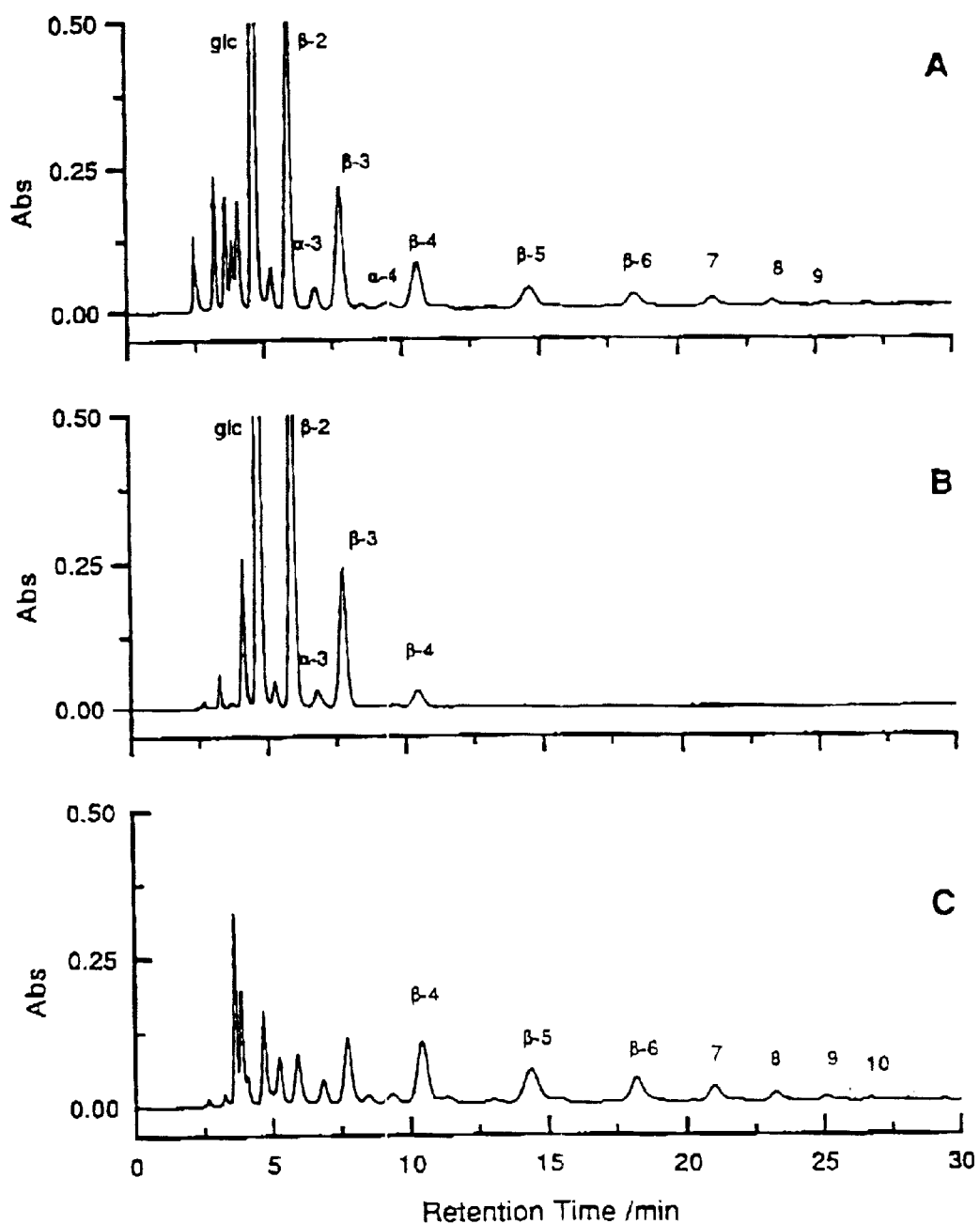
FIG. 5: HPLC chromatogram, using an aminopropyl column of the separation of a) the glycosyl pyrazoles prepared from the oligosaccharides present in commercial glucose (corn) syrup; b) the glycosyl pyrazoles which are eluted from a graphitised carbon cartridge by a 10% acetonitrile eluent; c) the glycosyl pyrazoles which are eluted from a graphitised carbon cartridge by a 25% acetonitrile eluent, after stepwise elution with water and 10% acetonitrile.

A mixture of glycan hydrazones of corn syrup was prepared using hydrazine and was converted to a mixture of glycosylpyrazole derivatives (FIG. 5a) by treatment with an excess of pentan-2,4-dione (acetylacetone) in aqueous solution. The reaction mixture was applied directly to a column or cartridge containing a carbon adsorbent. The reagent was removed by elution with water, while the glycosylpyrazoles were recovered by elution with 10% acetonitrile in water (DP 1 to 3) (FIG. 5b) and 25% acetonitrile in water (DP 3 to 10) (FIG. 5c). The recovery of the pyrazoles was monitored using an aminopropyl HPLC column (Rainin) with UV detection.

Desalting of Glucose Oligosaccharides from HPAEC

An oligosaccharide (BSW/6) from corn syrup was collected from a CarboPac PA1 HPLC column in approximately 0.5 mL of 0.2M sodium acetate in 0.25M sodium hydroxide. The fraction was applied directly to a column of graphitised carbon adsorbant, the column was washed with five bed volumes of water before the oligosaccharide was eluted with three bed volumes of 25% acetonitrile in water. The recovery of the desalted sugar was demonstrated by re-chromatography on the CarboPac PA1 HPLC column (FIG. 6).

Figure 7:
FIG. 7: HPAEC chromatogram of the re-chromatography of N-acetylneuraminyllactose obtained by preparative HPAEC and desalted using a graphitised carbon cartridge by elution of the salt with water and the oligosaccharide with 25% acetonitrile containing 0.05% trifluoroacetic acid.
Figure 8:
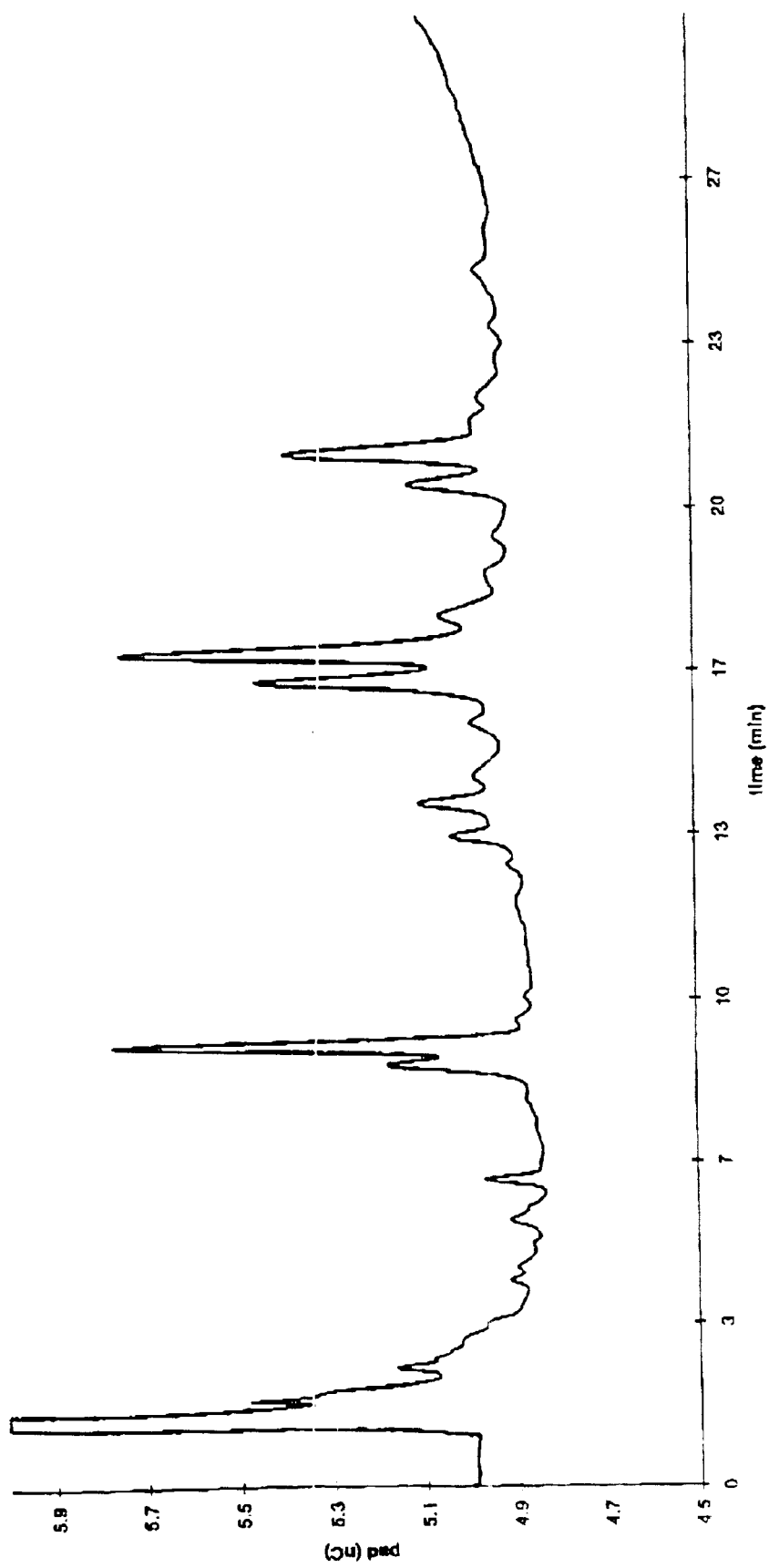

The acidic N-acetylneuraminyllactose was also separated from its isomers (FIG. 2) and collected from the CarboPac PA1 HPLC column. The fraction was applied directly to a column of graphitised carbon adsorbant, the column was washed with five bed volumes of water before the oligosaccharide was eluted with three bed volumes of 25% acetonitrile containing 0.05% TFA. The recovery of the desalted sugar was demonstrated by re-chromatography on the CarboPac PA1 HPLC column (FIG. 7).

Glycoprotein Analysis

Post-hydrazinolysis Clean Up

Anhydrous hydrazine is used for the removal of N- and O-linked oligosaccharides from glycoproteins. The hydrazine needs to be removed before the reducing terminus is regenerated. To date this has involved exhaustive paper chromatography or more recently cellulose chromatography has been incorporated, with mixed success by many workers, into marketed kits (Oxford GlycoSystems).

Hydrazine was shown to elute from the PGC cartridge with water. A model glycoprotein (1 mg bovine fetuin) was subjected to hydrazinolysis by heating in anhydrous hydrazine at 95° C. for 4 h. The hydrazine was removed by evaporation (SpeedVac, Savant), washed once with toluene to remove excess hydrazine, and the mixture of products was dissolved in 1 mL water, and applied to a small PGC column (1 mL bed volume). The column was eluted with five bed volumes of water to remove residual hydrazine, then with three bed volumes of water containing 25% acetonitrile to elute neutral glycans, then with the same eluent containing 0.05% trifluoroacetic acid to elute acidic glycans. Amino acid analysis of the fractions showed that the peptides resulting from the hydrazinolysis were eluted predominantly by 50% acetonitrile in water and in 0.05% TFA.

Figure 8:
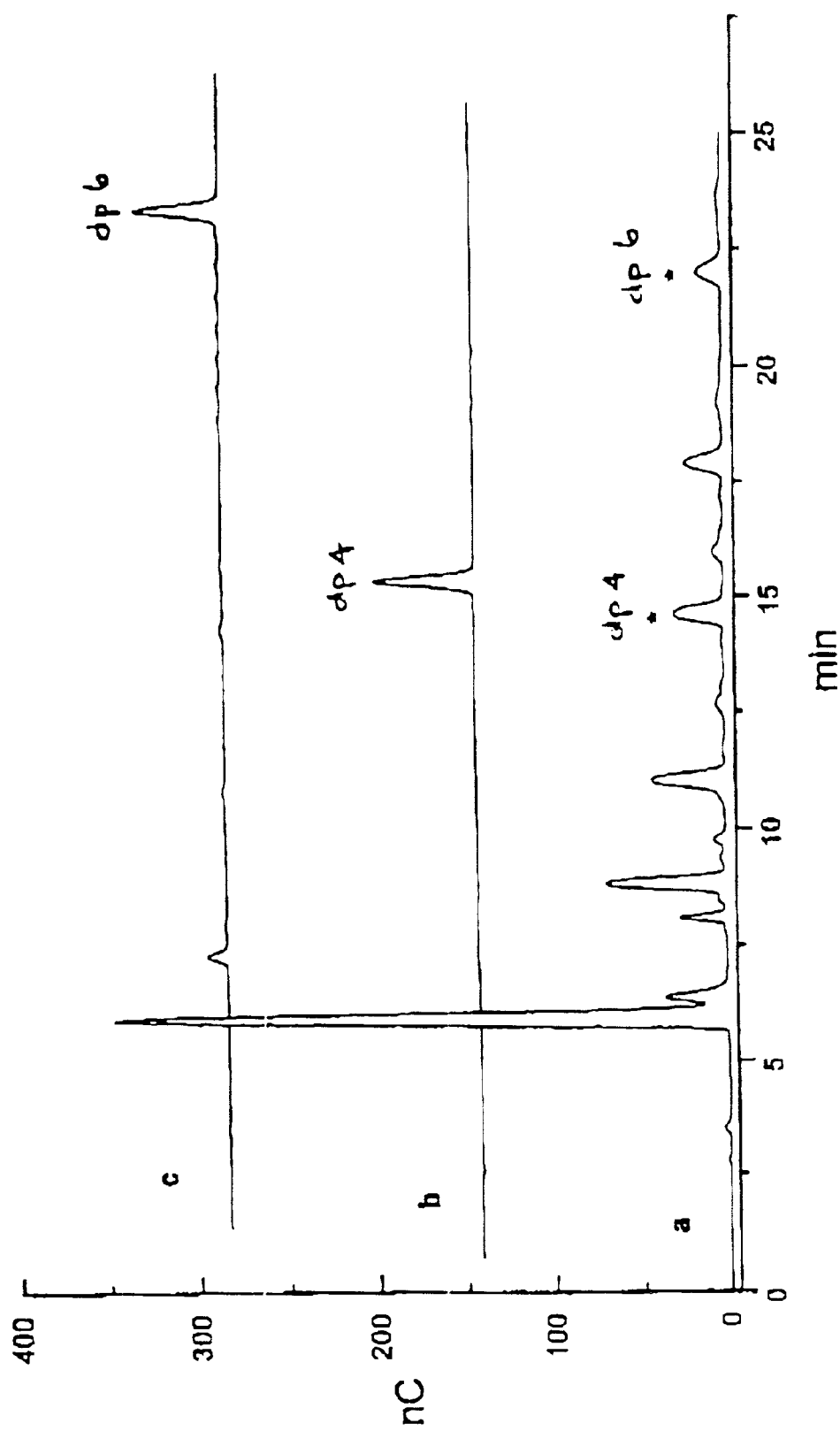
FIG. 8: HPAEC chromatogram of the oligosaccharides released from bovine fetuin by using anhydrous hydrazine and then desalting on a graphitised carbon cartridge. The salts were eluted with water and the oligosaccharides were eluted with 25% acetonitrile containing 0.05% trifluoroacetic acid. The desalted glycan hydrazones were acetylated, then converted to the reducing glycans by treatment with aqueous copper(II) acetate(7) to regenerate the reducing sugars.

The acetylated glycan hydrazones were prepared and converted to the reducing glycans by treatment with aqueous copper(II) acetate and the regenerated reducing sugars were separated on HPAEC (FIG. 8).

Desalting and Fractionation of Glycans Released by PNGase F.

Figure 9:
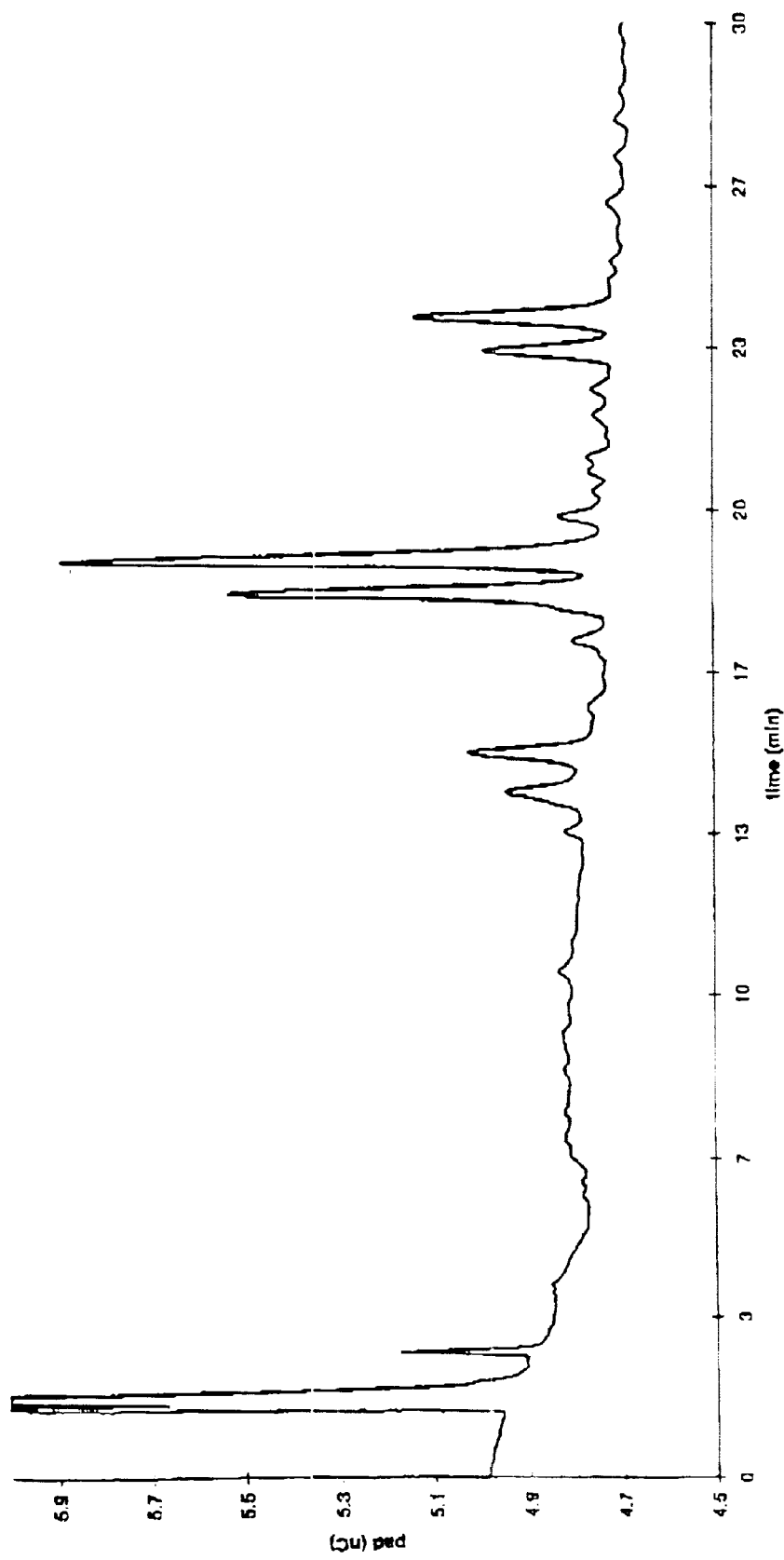
FIG. 9: HPAEC chromatogram of the oligosaccharides released from bovine fetuin by using PNGase and 0.05% reduced Triton X100 and then desalted on a graphitised carbon cartridge. The salts and detergent were eluted with water and the oligosaccharides were eluted with 25% acetonitrile containing 0.05% trifluoroacetic acid.
Figure 10:
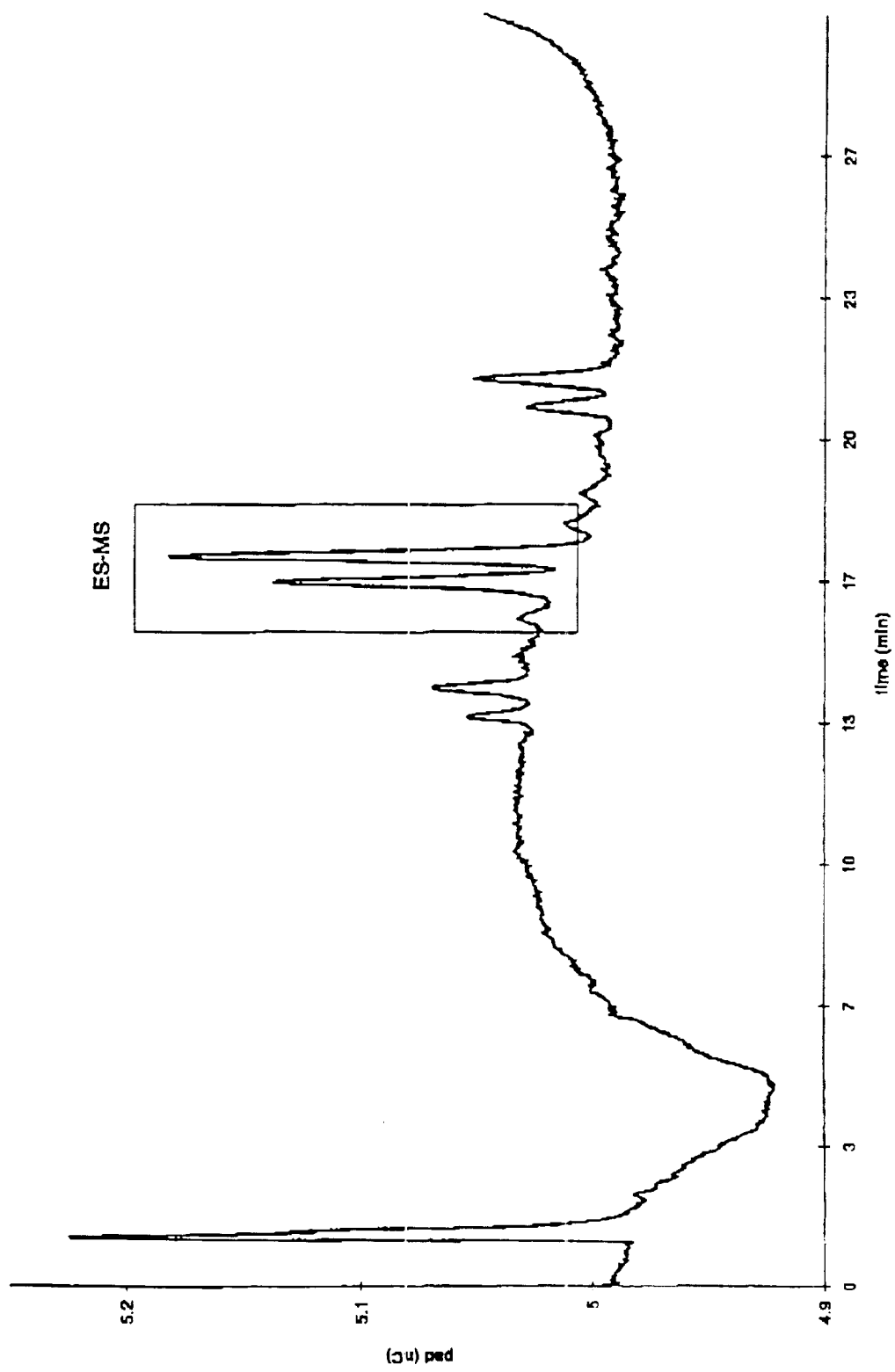
FIG. 10: HPAEC chromatogram of the oligosaccharides released from bovine fetuin by using PNGase and 0.1% SDS and then desalted on a graphitised carbon cartridge after the addition of excess NP40. The salts and detergents were eluted with water and the acidic oligosaccharides were eluted with 25% acetonitrile containing 0.05% trifluoroacetic acid.

The most commonly used method for releasing N-linked oligosaccharides from glycoproteins is the use of endoglycosidases such as PNGase F, Endo F and Endo H. The reaction is usually achieved with high yield by the denaturation of the glycoprotein by the action of detergents at high temperature to order to increase the accessibility of the enzyme to the glycosylated sites. Model glycoproteins (500 μg bovine fetuin consisting of 3 sites with acidic N-linked oligosaccharides; and ovalbumin comprising a single site of N-linked neutral oligosaccharide) were treated with peptide N-glycosidase F (5 units, PNGase F) in 100 mM phosphate buffer pH 7 containing 5 mM dithiothreitol to effect the release of asparagine-linked (N-linked) glycans. The enzyme reaction was carried out after denaturation of the protein with either 1) 0.05% reduced Triton X100 (FIG. 9) or 2) 0.1% SDS (FIG. 10). A five-fold excess of NP40 was added before the addition of enzyme in the latter. SDS is eluted from PGC in water, but in the presence of proteins which bind the SDS, the selectivity of the carbon column is changed. It is helpful that the NP40 or similar non-ionic detergent is added in excess prior to applying the sample to the PGC column to enable the water to wash out the SDS micelles which are presumably formed.

The incubation mixture is applied to a graphitised carbon column (1 mL bed volume). The column was eluted with five bed volumes to remove the buffer salts and detergents, then with three bed volumes of water containing 25% acetonitrile to elute neutral glycans, then with the same eluent containing 0.05% trifluoroacetic acid to elute acidic glycans. The acidic glycan profile obtained is shown (FIG. 9 and 10) and is a typical profile of the oligosaccharides released from fetuin.

This clean up of oligosaccharides released by PNGase has been applied successfully to the analysis of recombinant proteins produced by CHO cells and to the separation of the neutral and acidic oligosaccharides released from low density lipoprotein.

Adsorption of Protein (Deproteinisation of Solutions)

The fate of the deglycosylated protein was investigated by monitoring the behaviour of bovine serum albumin (a non-glycosylated protein) on the PGC cartridge. A solution of bovine serum albumin (BSA, 0.5 mg/mL) in 100 mM phosphate buffer (1 mL) was applied to a PGC cartridge. Monitoring of the fractions by UV absorption at 280 nm showed that no protein eluted using three bed volumes of 0, 25, 50, 100% acetonitrile or 0, 25, 50, 80% acetonitrile containing 0.1% TFA. Under these conditions all glycans can be eluted. The protein could not be desorbed from the column using 50% propanol, water-saturated butanol, butanol-saturated water, 1M ammonia, or 0.1M NaOH, as judged by the Bio-Rad DG protein assay. The PGC column can thus be used for deproteinising solutions of oligosaccharides.

Figure 11:
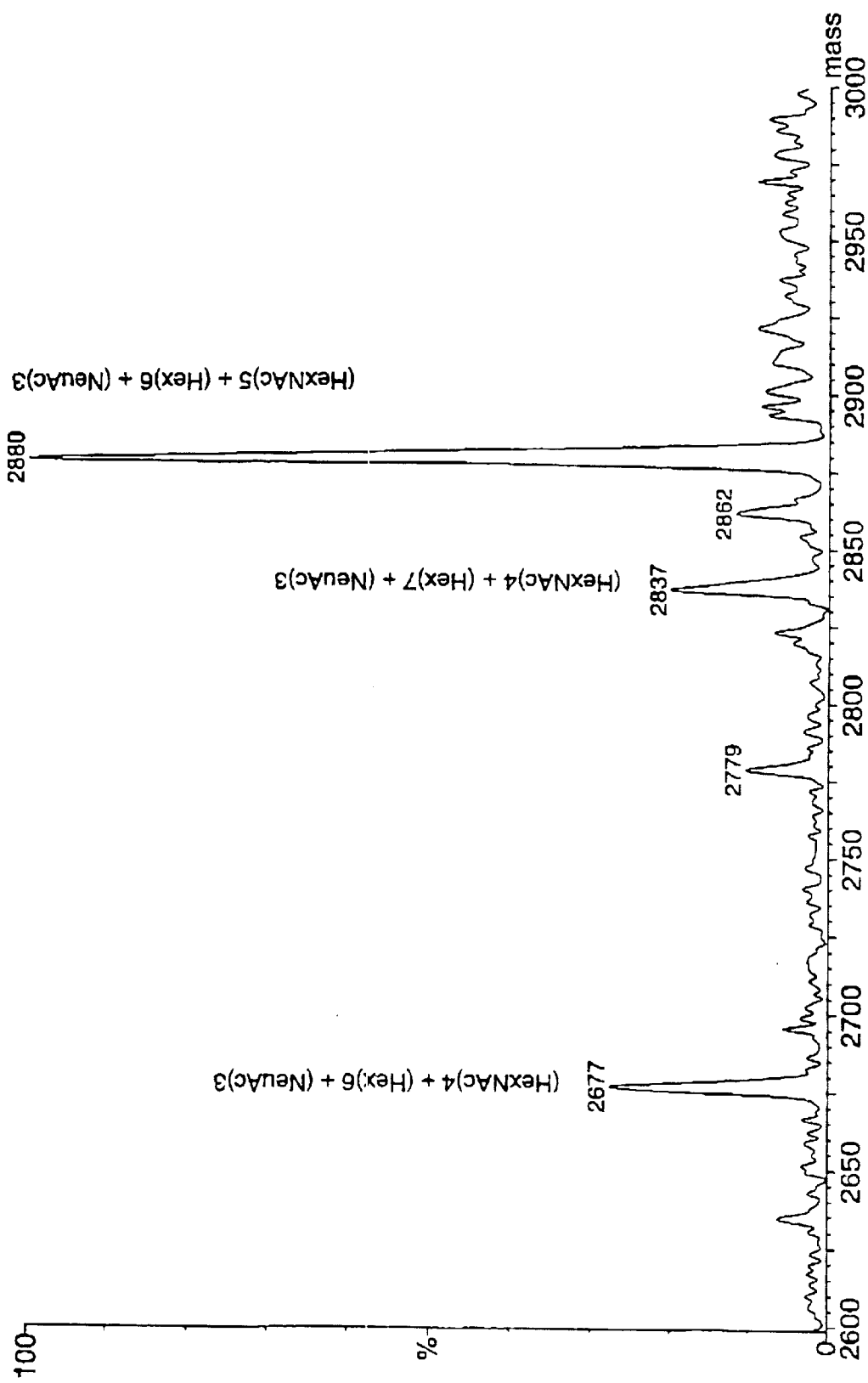
FIG. 11: Electrospray mass spectrum of trisialylated oligosaccharide isomers released enzymically from bovine fetuin. The isomers were collected from the HPAEC column and desalted using a graphitised carbon cartridge on-line to the mass spectrometer.

On-line Desalting of Oligosaccharides from High Pressure Anion Exchange Chromatography-HPAEC-PAD)-Application to ES-MS of Glycoprotein Oligosaccharides The oligosaccharides released enzymically from fetuin and ovalbumin were collected from the CarboPac PA1 HPLC column. The trisialylated oligosaccharide isomers of fetuin (see FIG. 10) were collected in approximately 0.5 mL of 0.2M sodium acetate in 0.25M sodium hydroxide and applied directly to a porous graphitised carbon on-line HPLC cartridge (0.5 mL bed volume). The cartridge was washed with five bed volumes of water before the oligosaccharides were eluted directly into the electrospray-masspectrometer with 25% acetonitrile in 0.05% TFA. The mass of the fetuin trisialylated oligosaccharide isomers was obtained (2879 mass) and the mass spectrum showed evidence of a small amount of peeling occurring in the alkaline chromatography as evidenced by the loss of mass equal to one N-acetylglucosamine moiety (FIG. 11). The recovery of the desalted sugar was also evidenced by re-chromatography on the CarboPac PA1 HPLC column.

Figure 12:
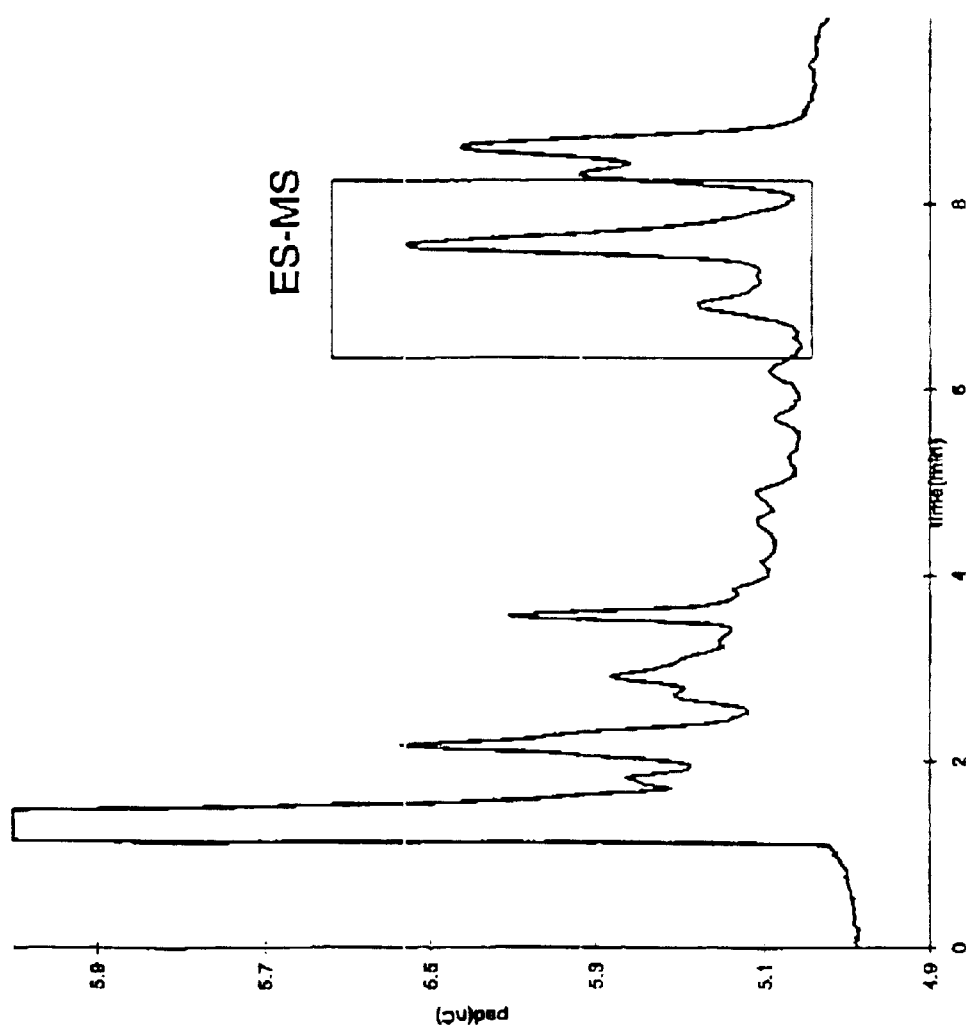
FIG. 12: HPAEC chromatogram of the oligosaccharides released from ovalbumin by using PNGase and 0.1% SDS and then desalted on a graphitised carbon cartridge after the addition of excess NP40. The salts and detergents were eluted with water and the neutral oligosaccharides were eluted with 25% acetonitrile.
Figure 13:
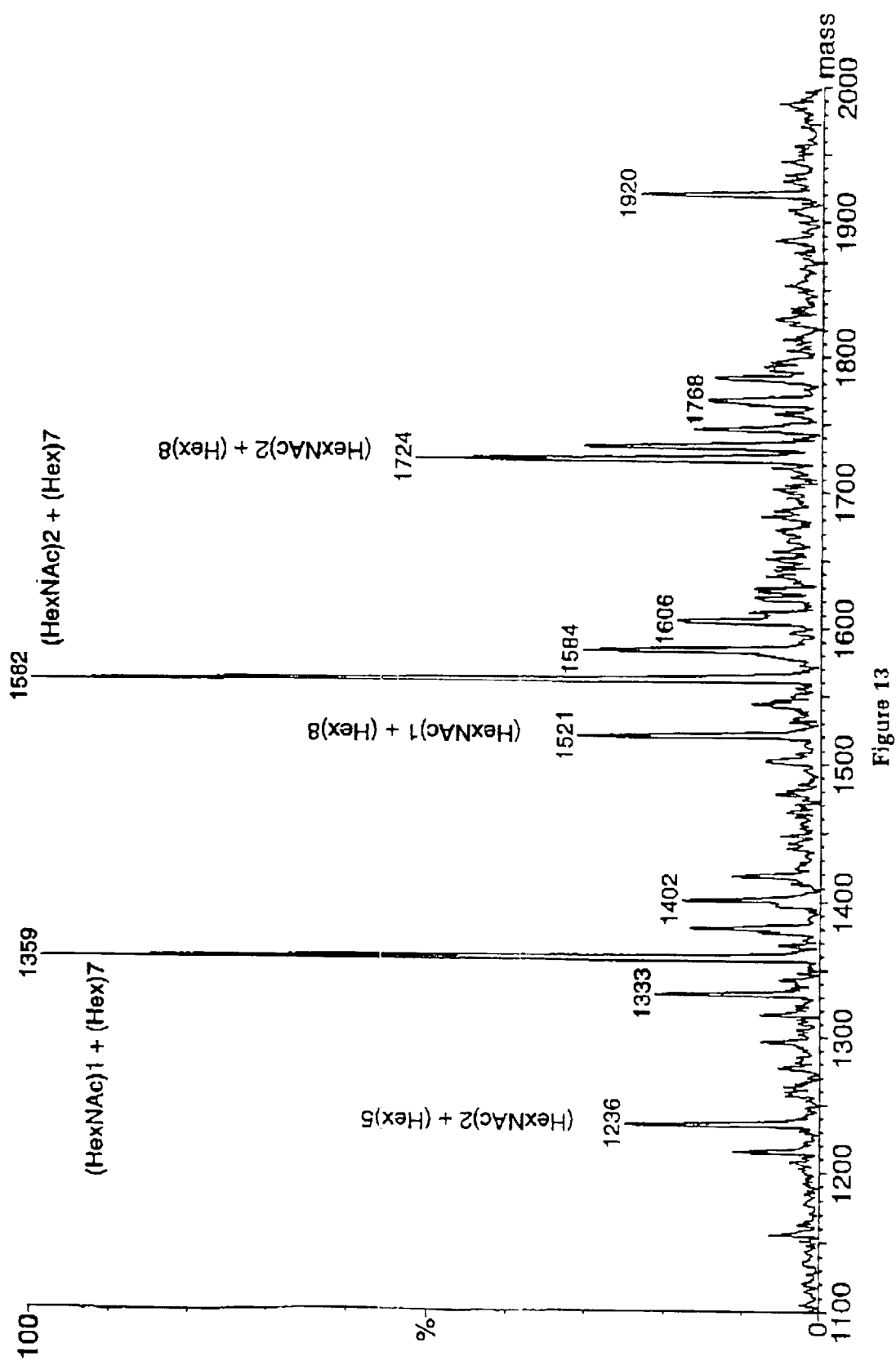
FIG. 13: Electrospray mass spectrum of oligosaccharides released enzymically from ovalbumin. The oligosaccharides were collected from the HPAEC column and desalted using a graphitised carbon cartridge on-line to the mass spectrometer.

The group of neutral oligosaccharides released enzymatically from ovalbumin (FIG. 12) were collected in approximately 1 mL of 0.1M sodium acetate in 0.25M sodium hydroxide and applied directly to a porous graphitised carbon on-line HPLC cartridge (0.5 mL bed volume). The cartridge was washed with five bed volumes of water before the oligosaccharides were eluted directly into the electrospray-masspectrometer with 25% acetonitrile in 0.05% TFA. The mass spectrum obtained shows the heterogeneity of the ovalbumin oligosaccharides (FIG. 13).

Fractionation After Release of Serine- and Threonine-linked Glycans of a Glycoprotein O-linked oligosaccharides are typically released chemically from glycoproteins by beta elimination. A model glycoprotein (bovine submaxillary mucin) was subjected to beta elimination in the presence of sodium hydroxide and sodium borohydride. The reaction was terminated by acidification with dilute acid and the solution was applied to a graphitised carbon cartridge. The cartridge was eluted with five bed volumes to remove salts, then three bed volumes of water/acetonitrile (3:1) containing 0.05% trifluoroacetic acid to elute the glycans. Monosaccharide analysis before and after β-elimination showed 99% recovery of the oligosaccharides from the PGC column.

Desalting and Deproteinisation of Urine Prior to Oligosaccharide Analysis

Figure 14:
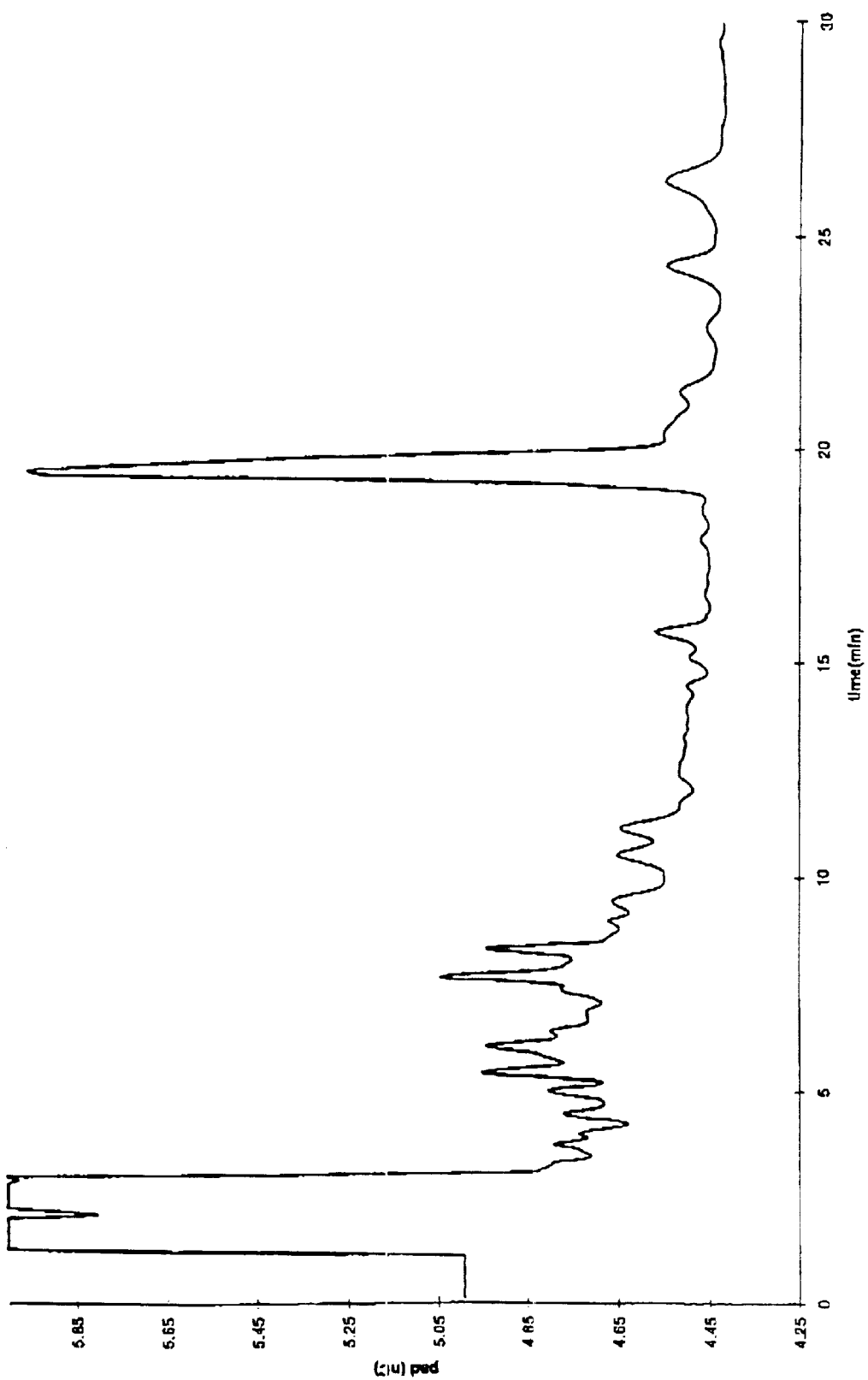
FIG. 14: HPAEC chromatogram of the oligosaccharides accumulated in the urine of a patient with mucopolysaccharidosis disease (GM1). The urine was desalted using a graphitised carbon column and the oligosaccharides were eluted in 25% acetonitrile prior to chromatographic analysis.

Urine containing oligosaccharides which accumulate in the mucopolysaccharidosis disease (GM1), was desalted prior to analysis by HPAEC-PAD. A sample of 5 mL of urine was applied to the PGC column, the salts were washed off with water and the oligosaccharides were eluted with 25% acetonitrile. The eluted sugars were dried in a Speed-Vac, redissolved in water and applied directly to the chromatography column. The results are shown in FIG. 14 and demonstrate the application of this desalting method to biological fluids.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Whistler R L. and BeMiller J N. *Methods in Carbohydrate Chemistry,* Vol. 1 (1962) (Ed. Whistler R L & Wolfrom M L) APress, N.Y. pp. 42–44
2. Knox, J H, Kaur, B. and Millward *J. Chromatogr.,* 352 (1986) 3–25.
3. Koizumi, K., Okada, Y. and Fukuda M. *Carbohydr. Res* 215 (1991) 67–80
4. Davies, M., Smith K. D., Harbin, A. and Hounsell, E F. *J. Chromatogr.,* 609 (1992) 125–131.
5. Davies, M., Smith, K D., Carruthers. R A., Chai, W., Lawson, A M. and Hounsell, E F. *J. Chromatogr.,* 646 (1993) 317–326.
6. Fan, J Q., Kondo, A., Kato, I. and Lee Y C. *Anal. Biochem.* 219 (1994) 224–229
7. Patel, T., Bruce, J., Merry, A., Bigge, C., Wormald, M., Jaques, A. and Parekh, R. *Biochemistry,* 32(1993) 679–693
8. Bertolini, M. and Pigman, W. *J.Biol. Chem.* 242 (1967) 3776
9. Cooper C A., Packer, N H. and Redmond, J W. *Glycoconjugate J.* (1994) 11, 163–167
10. Tweeddale, H J., Batley, M and Redmond, J W. *Glycoconjugate J.* (1994) 11, 586–592

What is claimed is:

1. A preparative non-high pressure, liquid chromatography (LC) method of separating oligosaccharides from salts in a sample, which method consists essentially of the steps of:

(a) reacting a sample containing oligosaccharides and salt contaminants with a solid support comprising carbon such that the oligosaccharides substantially bind to the solid LC support;

(b) washing the support to remove any salt contaminants not bound to the solid support; and (c) eluting the bound oligosaccharides from the support as mixtures without eluting bound salt contaminants to obtain a solution of oligosaccharides substantially free of salt contaminants.

2. The method according to claim 1 wherein the salts are selected from the group consisting of sodium chloride, potassium chloride, caustic alkali, cationic buffers, anionic buffers, zwitterionic buffers and surfactants.

3. The method according to claim 2 wherein the salts are selected from the group consisting of sodium hydroxide, Tris, phosphate, acetate, HEPES, MOPS, and sodium dodecyl sulfate (SDS).

4. The method of claim 1 wherein the solid support comprises graphitised carbon.

5. The method of claim 1 wherein the support is packed in a chromatography column or cartridge.

6. The method according to claim 1 wherein the washing step (b) utilizes water and the elution step (c) utilizes water and an organic modifier.

7. The method of claim 6 wherein the organic modifier is acetonitrile.

8. The method according to claim 7 wherein the concentration of the organic modifier is from 1 to 90% v/v.

9. The method of claim 6 wherein the organic modifier is selected from the group consisting of methanol, ethanol, propanol and butanol.

10. The method according to claim 9 wherein the concentration of the organic modifier is from 1 to 90% v/v.

11. The method according to claim 1 wherein the elution step (c) further utilizes acidic or basic modifiers.

12. The method according to claim 11 wherein the acidic modifier is a dilute acid.

13. The method according to claim 12 wherein the dilute acid is trifluoroacetic acid.

14. The method according to claim 13 wherein the concentration of the trifluoroacetic acid is 0.01 to 1% v/v.

15. The method according to claim 11 wherein the concentration of the acidic or basic modifier is 0.01 to 5% v/v.

16. The method of claim 1 wherein the salt contaminants further contain contaminants selected from the group consisting of detergents, reagents for the release of oligosaccharides from glycoconjugates, and reagents used for the formation of oligosaccharide derivatives.

17. The method of claim 16 wherein the reagents for the release of oligosaccharides from glycoconjugates are selected from the group consisting of hydrazine and sodium borohydride.

18. The method of claim 16 wherein the reagents used for the formation of oligosaccharide derivatives are aromatic amines.

* * * * *